United States Patent [19]

Cooker et al.

[11] Patent Number: 5,780,657
[45] Date of Patent: Jul. 14, 1998

[54] PROPYLENE EPOXIDATION USING CHLORIDE-CONTAINING SILVER CATALYSTS

[75] Inventors: Bernard Cooker, Malvern; Anne M. Gaffney, West Chester; Jennifer D. Jewson, Pottstown; Wilson H. Onimus, Holmes, all of Pa.

[73] Assignee: Arco Chemical Technology, L.P., Greenville, Del.

[21] Appl. No.: 880,905

[22] Filed: Jun. 23, 1997

[51] Int. Cl.$^6$ ............................................. C07D 301/10
[52] U.S. Cl. ................................... 549/534; 549/536
[58] Field of Search ............................ 549/534, 536

[56] References Cited

U.S. PATENT DOCUMENTS

| | | | |
|---|---|---|---|
| 2,177,361 | 10/1939 | Carter | 260/348 |
| 2,219,575 | 10/1940 | McNamee et al. | 260/348 |
| 2,615,900 | 10/1952 | Sears, Jr. | 260/348.5 |
| 2,709,173 | 5/1955 | Brengle et al. | 260/348.5 |
| 2,769,016 | 10/1956 | Lichtenwalter et al. | 260/348.5 |
| 2,799,687 | 7/1957 | Gould et al. | 260/348.5 |
| 3,132,157 | 5/1964 | Hermann et al. | 260/348.5 |
| 3,132,158 | 5/1964 | Hermann et al. | 260/348.5 |
| 3,585,217 | 6/1971 | Titzenthaler | 260/348.5 |
| 3,888,889 | 6/1975 | Kolombos et al. | 260/348.5 |
| 4,130,570 | 12/1978 | Boreskov et al. | 260/348.5 |
| 4,415,476 | 11/1983 | Ayame et al. | 502/224 |
| 4,950,773 | 8/1990 | Monnier et al. | 549/534 |
| 5,187,140 | 2/1993 | Thorsteinson et al. | 502/348 |
| 5,625,084 | 4/1997 | Pitchai et al. | 549/536 |

FOREIGN PATENT DOCUMENTS

| | | |
|---|---|---|
| 1282772 | 4/1991 | Canada. |
| 0207541 | 1/1987 | European Pat. Off.. |
| 1327497 | 8/1973 | United Kingdom. |
| 1338901 | 11/1973 | United Kingdom. |
| WO9505896 | 3/1995 | WIPO. |

*Primary Examiner*—Ba K. Trinh
*Attorney, Agent, or Firm*—Stephen D. Harper

[57] ABSTRACT

Direct oxidation of propylene to propylene oxide is accomplished using alkaline earth metal compound-supported silver catalysts containing an inorganic chloride promoter and a potassium promoter derived from a potassium salt containing a nitrogen oxyanion or precursor thereof.

15 Claims, No Drawings

PROPYLENE EPOXIDATION USING CHLORIDE-CONTAINING SILVER CATALYSTS

FIELD OF THE INVENTION

This invention relates to a process for the direct oxidation of propylene to propylene oxide in the vapor phase using molecular oxygen. In particular, the invention pertains to the use of compositions comprised of metallic silver supported on certain alkaline earth metal-containing compounds to selectively catalyze the formation of epoxides. The performance of the catalysts is improved by incorporating an inorganic chloride promoter such as silver chloride together with a potassium promoter derived from a potassium salt comprising potassium cation and a nitrogen oxyanion or precursor thereof.

BACKGROUND OF THE INVENTION

The direct oxidation of ethylene to ethylene oxide by molecular oxygen is well-known and is, in fact, the method used currently for commercial production of ethylene oxide. The typical catalyst for such purpose contains metallic or ionic silver, optionally modified with various promoters and activators. Most such catalysts contain a porous, inert support or carrier such as alpha alumina upon which the silver and promoters are deposited. A review of the direct oxidation of ethylene in the presence of supported silver catalysts is provided by Sachtler et al. in *Catalyst Reviews: Science and Engineering*, 23 (1&2), 127–149 (1981).

It is also well-known, however, that the catalysts and reaction conditions which are best suited for ethylene oxide production do not give comparable results in the direct oxidation of higher olefins such as propylene. The discovery of processes capable of providing propylene oxide by vapor phase direct oxidation in higher yields than are presently attainable thus would be most desirable.

Workers in the field have recognized for a number of years that the efficiency of a direct propylene epoxidation process catalyzed by a supported silver catalyst may be improved by introducing relatively small amounts of both a nitrogen oxide species such as NO and a volatile organic chloride such as ethyl chloride to the feedstream containing propylene and oxygen. See for example, U.S. Pat. No. 5,387,751 (Hayden et al.) and Canadian Pat. Nos. 1,282,772 (Thorsteinson) and 1,286,687 (Habenschuss et al.).

However, the addition of volatile organic chlorides into the feedstream has certain practical disadvantages. The use of an organic chloride, even at the ppm levels typically employed, adds significantly to the raw material costs associated with producing propylene oxide. Measures must be implemented to recover or trap any organic chloride in the effluent exiting the epoxidation reactor. Such recovery methods may involve the generation of ionic chloride species, which tend to accelerate corrosion of the construction materials used in the recovery section. Additionally, recovery of organic chloride is not always quantitative; unreacted or unhydrolyzed organic chlorides thus may escape from the process, contributing to air pollution.

Thus, it is readily apparent that the development of direct propylene epoxidation processes which do not require the addition of organic chlorides to the feedstream but which give satisfactorily high selectivity to propylene oxide would fulfill a great need in the field.

SUMMARY OF THE INVENTION

A process for propylene epoxidation is provided wherein a feedstream comprising propylene and oxygen is contacted with a particular type of silver catalyst. The catalyst is comprised of (a) a support; (b) a catalytically effective amount of metallic silver; (c) a promoting amount of an inorganic chloride promoter, and (d) a promoting amount of a potassium promoter. The support is comprised of an alkaline earth metal compound selected from the group consisting of alkaline earth metal carbonates (e.g., calcium carbonate), alkaline earth metal titanates, and mixtures thereof. The inorganic chloride promoter may be derived from an inorganic chloride compound such as silver chloride or an alkaline earth metal chloride. The potassium promoter is derived from a potassium salt such as potassium nitrate which comprises potassium cation and a nitrogen oxyanion or precursor thereof.

The process described herein is capable of producing propylene oxide at remarkably high selectivity and productivity even in the absence of organic chlorides in the feedstream.

DETAILED DESCRIPTION OF THE INVENTION

The present invention is directed to a process for the vapor phase oxidation of propylene to propylene oxide, i.e., an epoxidation process performed in the presence of an oxygen-containing gas and a particular class of supported silver catalysts.

The support material used in the present invention is an alkaline earth metal compound selected from alkaline earth metal carbonates, alkaline earth metal titanates, and mixtures thereof. Carbonates suitable for use include inorganic carbonates having a cation which is an alkaline earth metal ion, particularly calcium, strontium, magnesium or barium, with calcium carbonate being most preferred. Alkaline earth metal carbonate supports are described, for example, in Canadian Pat. No. 1,282,772. Alkaline earth metal titanates comprise the class of inorganic substances containing an alkaline earth metal such as barium, strontium, calcium, or magnesium and a titanate species. Suitable alkaline earth metal titanates thus may correspond to the empirical formula $MTiO_3$, $M_2TiO_4$, and $MTi_2O_5$ wherein M preferably=Ba, Sr, Ca, or Mg. Any of the conventional methods for preparing such substances may be utilized. Barium titanate, for example, may be prepared by heating a mixture of the correct proportions of barium carbonate and titanium dioxide at 1300° C. until the reaction is complete. Strontium titanate may be obtained in pure form by calcining the double strontium titanium oxalate precipitate from titanium tetrachloride solution. The calcium titanate can correspond to the compound $CaTiO_3$ (CAS 12049-50-2), which occurs naturally as the mineral perovskite, but which can also be synthesized by heating equimolar amounts of the oxide to 1350° C. The term "calcium titanate" as used herein also embraces the substances having the formula $3CaO.2TiO_2$ (CAS 12013-80-8) and $3CaO.TiO$ (CAS 12013-70-6). Magnesium titanates include the metatitanate $MgTiO_3$, the orthotitanate $Mg_2TiO_4$, and the dititanate $MgTi_2O_5$.

Such support materials are capable of providing exceptionally high propylene oxide selectivities and have been found to be surprisingly superior to other support materials in this respect. The carriers of the present invention may exist in various forms. In one embodiment, the carrier is one in which the alkaline earth metal compound is the predominant (i.e., at least 50% by weight) or, preferably, substantially the exclusive component of the support (i.e., the support consists essentially of one or more alkaline earth metal compounds). In other embodiments of the invention, the inorganic support material is used in conjunction with a solid substrate, i.e., a subsupport or substructure composed of a more conventional support material, such as alumina (preferably, alpha-alumina). However, the alkaline earth metal compound support material will normally comprise at least 25 weight percent (in most embodiments, at least 35 weight percent) of the finished catalyst.

The surface area of the alkaline earth metal compound support material generally is at least 0.6 m$^2$/g, preferably at least 1.5 m$^2$/g. However, alkaline earth metal compound support materials having relatively high surface areas (e.g., 50 to 100 m$^2$/g) are also effective for the purposes of this invention. This result was surprising in view of the preference generally expressed in the direct olefin oxidation field for low surface area supports (typically, 0.03 to 10 m$^2$/g). The surface area is measured by the conventional B.E.T. method using nitrogen or krypton described by Brunauer, Emmett and Teller in *J. Am. Chem. Soc.* 60, 309–16 (1938).

The support materials used in the present invention may generally be described as porous or microporous and typically have water pore volumes of about 0.05 to 0.80 cc/g.

The supported catalyst of the present invention may be prepared by any known method of introducing silver and/or a promoter in soluble form to a support. A preferred method of introducing silver to the alkaline earth metal compound support is by an impregnation process in which a solution of a silver compound (which can be a salt or complex of silver) in an amount sufficient to deposit the desired weight of silver upon the support is dissolved in a suitable solvent or "complexing/solubilizing" agent. The solution may be used to impregnate the support by immersing the support in the silver compound-containing impregnating solution and forming a pasty mixture or slurry. The slurry is then dried and calcined by placing the mixture in an oven or furnace at about 100° to about 120° C. for 0.5 to 6 hours and then heating the mixture at a temperature of from about 250° to about 600° C. for another 1 to 6 hours. This procedure accomplishes drying of the alkaline earth metal compound/silver mixture, removes volatile components and reduces the silver compound present to its elemental form.

The potassium salt and inorganic chloride compound may be introduced to the catalyst, either simultaneously or separately, as impregnation solutions in a separate impregnation step or steps. Again, this may be done by any known manner of impregnating a porous material. Conveniently, this may be carried out by placing the catalyst material in a container, evacuating the container and thereafter introducing the solution(s). Alternatively, the support may be sprayed or sprinkled with the impregnating solution(s). The excess solution may then be allowed to drain off or the solvent may be removed by evaporation under reduced pressure at a suitable temperature. The catalyst may then be dried at a moderate temperature (e.g., at 120° C.) in a oven for one-half to five hours and/or calcined at a higher temperature in between the impregnation steps. Such a procedure is known as a "sequential" or "consecutive" method of preparation. In one such embodiment, the support is impregnated with only the inorganic chloride compound and the silver compound, dried, calcined, and then impregnated with a solution of the potassium salt, followed by drying. The alkaline earth metal compound-supported catalyst may also be prepared by a "simultaneous" or "coincidental" method of preparation. With this method, the potassium promoter and the inorganic chloride compound are included in the silver compound-containing solution used to impregnate the support.

The choice of silver compound used to form the silver-containing impregnating solution in a solvent or a complexing/solubilizing agent is not particularly critical and any silver compound generally known to the art which is both soluble in and does not react with the solvent or complexing/solubilizing agent to form an unwanted product and which may be converted to metallic silver may be employed. Thus, the silver may be introduced to the solvent or complexing/solubilizing agent as an oxide or a salt, such as nitrate, carbonate, or carboxylate, for example, an acetate, propionate, butyrate, oxalate, malonate, malate, maleate, lactate, citrate, phthalate, fatty acid ester, and the like or combinations thereof. In one embodiment, silver (I) oxide is utilized. Combinations of one or more silver compounds easily reduced to metallic form under calcination conditions (e.g., silver oxide and silver carboxylates) together with silver chloride (which is not readily reduced to silver metal and thus may serve as a source of the inorganic chloride promoter in the catalyst) may also be used to advantage. Surprisingly, the silver chloride need not be applied to the support in the form of a solution in order to obtain an active and selective catalyst. Thus, the silver chloride may be in the form of a suspension or slurry or combined directly with the support as a dry solid.

A large number of solvents or complexing/solubilizing agents may be suitably used to form the silver compound-containing impregnating solution. Besides adequately dissolving the silver compound or converting it to a soluble form, a suitable solvent or complexing/solubilizing agent should be capable of being readily removed in subsequent steps, either by a washing, volatilizing or oxidation procedure, or the like. The complexing/solubilizing agent, preferably, should also permit solution to provide metallic silver in the finished catalyst to the extent of preferably about 10 to about 60 percent metallic silver, based on the total weight of the catalyst. It is also generally preferred that the solvents or complexing/solubilizing agents be readily miscible with water since aqueous solutions may be conveniently employed. Among the materials found suitable as solvents or complexing/solubilizing agents for the preparation of the silver compound-containing solutions are alcohols, including glycols, such as ethylene glycol, amines (including alkanolamines such as ethanolamine and alkyldiamines such as ethylenediamine) and carboxylic acids, such as lactic acid and oxalic acid, as well as aqueous mixtures of such materials.

Typically, a silver compound-containing solution is prepared by dissolving a silver compound in a suitable solvent or complexing/solubilizing agent such as, for example, a mixture of water, ethylenediamine, oxalic acid, silver oxide, and mono-ethanolamine. The solution is then mixed with support particles and drained. Thereafter the particles are suitably dried.

As indicated above, after impregnation, the silver compound-impregnated support particles are treated to convert at least a portion of the silver compound to silver metal and thereby effect deposition of silver on the surface of the support. As used herein, the term "surface", as applied to the support, includes not only the external surfaces of the support but also the internal surfaces, that is, the surfaces defining the pores or internal portion of the support particles. This may be done by treating the impregnated particles with a reducing agent, such as hydrogen or hydrazine and/or by roasting, at an elevated temperature to decompose the silver compound and reduce the silver to its free metallic state. Certain solubilizing agents such as alkanolamines, alkyldiamines, and the like may also function as reducing agents.

Although at least a catalytically effective amount of metallic silver must be present in the finished catalyst (meaning an amount that provides a measurable conversion of propylene to propylene oxide), the metallic silver concentration preferably is from about 2 percent to 70 percent, by weight, based on the total weight of the catalyst. More preferably, the metallic silver concentration ranges from about 10 to 60 percent by weight. In certain embodiments of the invention, silver in non-metallic form may also be present in the finished catalyst; for example, the catalyst may contain 0.1 to 5 weight percent silver chloride.

It has been unexpectedly discovered that the presence of potassium in the preparation of the supported silver catalyst significantly enhances the efficiency of said catalyst as a propylene epoxidation catalyst. Surprisingly, other alkali metals such as cesium which are well-known as promoters in the ethylene oxide art fail to improve catalyst performance to an appreciable extent. The potassium is introduced by means of a potassium salt, with the selection of particular anions as counter ions to the potassium cation being found to be critical to the attainment of optimum catalyst performance. A nitrogen oxyanion such as nitrate, nitrite, or other negative ion containing both nitrogen and oxygen atoms thus may serve as the anion. Potassium compounds containing species capable of being converted to nitrogen oxyanions under the catalyst preparation or epoxidation conditions (i.e., which are nitrogen oxyanion precursors) are also suitable for use. For example, carbonates of potassium may be used to prepare the catalyst, with the catalyst being exposed to NO or another nitrogen oxygen species at an elevated temperature during a preconditioning step or during epoxidation. Preferred potassium salts include potassium nitrate, potassium nitrite, potassium carbonate, potassium bicarbonate, and mixtures thereof.

The efficiency-enhancing potassium salt may be introduced to the catalyst in any known manner. Thus, impregnation and deposition of a silver compound and the potassium salt may be effected coincidentally or sequentially. For example, the support could be impregnated with a solution or solutions of the potassium salt and silver compound, dried, and then calcined to reduce the silver compound and generate the active supported silver catalyst. Alternatively, the potassium salt may be introduced into a catalyst which has already been impregnated with silver compound, dried, and calcined.

In order to perform coincidental impregnation, the potassium salt must be soluble in the same solvent or complexing/ solubilizing agent used with the silver compound impregnating solution. With a sequential procedure in which the silver compound is added first, any solvent capable of dissolving the salt which will neither react with the silver compound nor leach it from the support is suitable. Aqueous solutions are generally preferred, but organic liquids, such as alcohols, may also be employed. Suitable procedures for effecting introduction of a potassium salt to a solid support are well known in the art.

The potassium salt is used in an amount sufficient to provide a potassium promoter concentration which results in an improvement in one or more of the catalytic properties (e.g., selectivity, activity, conversion, stability, yield) of the supported silver catalyst as compared to a catalyst not containing the potassium promoter. The precise amount will vary depending upon such variables as the composition in the feed stream, the amount of metallic silver and inorganic chloride promoter contained in the catalyst, the surface area of the support, the process conditions, e.g., space velocity and temperature, and morphology of support. It has been found, however, that a minimum of at least 0.1 percent by weight of the potassium promoter, calculated as cation, based on the total weight of the catalyst must be present for the catalyst to exhibit a significant advantage over an analogous catalyst containing no potassium promoter. Potassium concentrations as high as 10 percent by weight may be utilized, although generally little additional benefit is realized beyond a concentration of 5 weight percent. More preferably, the potassium promoter level is an amount corresponding to about 0.5 to about 3 weight percent K.

The other necessary component of the alkaline earth metal compound-supported silver catalysts of this invention is a promoting amount of an inorganic chloride promoter. Other promoters including metal promoters such as Mo, W, Re and the like may also be present, but the catalyst is capable of operating at relatively high activity and selectivity even when essentially free of such other substances. "Promoting amount" means an amount that works effectively to provide an improvement in one or more catalytic properties of a catalyst as compared to a catalyst not containing an inorganic chloride promoter. The exact form of the inorganic chloride promoter under epoxidation operating conditions is not known.

In general, the choice of inorganic chloride compound utilized as a source of the inorganic chloride promoter is not regarded as critical, although the introduction of substances known to be poisons for supported silver oxidation catalysts should be avoided. Exemplary classes of inorganic chloride compounds suitable for use in the present invention include, but are not limited to, alkali metal chlorides (e.g., potassium chloride, sodium chloride), alkaline earth metal chlorides (e.g., magnesium chloride, barium chloride, calcium chloride), and transition metal chlorides (e.g., silver chloride, molybdenum pentachloride, tungsten pentachloride, rhenium pentachloride). In a particularly desirable embodiment of the invention, a combination of silver chloride (which functions as a source of the inorganic chloride promoter) and a silver compound capable of being transformed into metallic silver under the catalyst preparation conditions is utilized.

The support is impregnated or otherwise combined with one or more inorganic chloride compounds. This may be done at the same time that the other components of the catalyst are added or before and/or later. In one advantageous and convenient embodiment of the invention, the inorganic chloride compound, potassium salt and silver compound are incorporated into the catalyst simultaneously. In another desirable embodiment, the potassium salt is introduced after calcination of an impregnated support containing the silver compound and the inorganic chloride compound.

The inorganic chloride compound may be applied to the catalyst in the form of a solution or, alternatively, as a solid. Where the inorganic chloride compound is soluble in the same solvent used to form impregnating solutions of the silver compound and/or potassium salt, for example, it will often be convenient to use an impregnation technique to introduce the inorganic chloride compound into the catalyst. Such impregnation may be performed in either a sequential or coincidental manner with respect to silver compound or potassium salt impregnation. When the compound is applied as a solid, it is generally desirable to use a finely divided form of the inorganic chloride compound and/or to grind, ball mill or otherwise intimately admix the components of the catalyst so as to achieve a relatively disperse and uniform distribution of the inorganic chloride compound with the support.

It has been found that the minimum amount of inorganic chloride promoter present in or deposited on the support or catalyst needed to measurably improve catalyst performance is 0.05 weight percent Cl (measured as the element irrespective of the form in which the promoter is present) based on the total weight of the supported silver catalyst. Generally speaking, the maximum amount of inorganic chloride promoter will be 2 weight percent. Operation within the range of 0.1 to 1.5 weight % Cl is particularly advantageous.

The degree of benefit obtained within the above-defined limits will vary depending upon particular properties and characteristics, such as, for example, reaction conditions, catalyst preparative techniques, surface area and pore structure and surface chemical properties of the support utilized, silver content of the catalyst, and potassium content of the catalyst.

The presence of the indicated and claimed amounts of inorganic chloride promoter in this specification and claims does not preclude the use of other activators, promoters, enhancers, stabilizers, improvers, and the like.

In the epoxidation process of this invention, propylene and an oxygen-containing gas (i.e., a gas comprising molecular oxygen) are brought together in a reactor in the presence of the previously described catalyst under conditions effective to accomplish at least partial oxidation of the propylene to the corresponding epoxide. Typical epoxidation conditions include temperatures within the reaction zone of the reactor on the order of about 180° to 320° C. (more preferably, 200° to 300° C., most preferably, 220° to 280° C.) and pressures from about 1 to about 60 atmospheres. To favor high selectivity to epoxide, it is desirable that the feedstream contain carbon dioxide. A gaseous nitrogen oxide species (described in more detail hereafter) is also desirably supplied to the reaction zone within the reactor by introducing said species to the feedstream containing propylene (fresh and/or recycled) and molecular oxygen, particularly where the catalyst is prepared by a procedure other than one in which potassium nitrate is added to the catalyst after calcination. While an organic halide such as ethyl chloride could also be present in the feedstream, satisfactory results may be obtained in the absence of any organic halide. Thus, in a preferred embodiment of the invention, the concentration of organic halide in the feedstream is essentially zero (i.e., <1 ppm).

Examples of nitrogen oxide species suitable for introduction in the feedstream include at least one of NO, $NO_2$, $N_2O_4$, $N_2O_3$ or any gaseous substance capable of forming one of the aforementioned gases, particularly NO and $NO_2$, under epoxidation conditions, and mixtures of one of the foregoing, particularly NO, with one or more of CO, $PH_3$, $SO_3$ and $SO_2$. NO is the most preferred nitrogen oxide species.

The amount of gaseous nitrogen oxide species present is not critical, although it will often be advantageous, depending upon the specific catalyst composition and epoxidation conditions selected, to expose the catalyst to the nitrogen oxide species either prior to use (as a preconditioning step) or while being used in the epoxidation process. The optimum amount is determined, in part, by the particular potassium salt, inorganic chloride compound and optional metal promoter(s) used and the concentrations thereof, and by other factors noted above which influence the optimum amount of potassium salt and inorganic chloride promoter. Typically, a suitable concentration of the nitrogen oxide species for epoxidation of propylene is about 0.1 to about 2,000 ppm by volume, when $N_2$ is used as a ballast.

The "oxygen" employed in the reaction may be defined as including pure molecular oxygen, atomic oxygen, any transient radical species derived from atomic or molecular oxygen capable of existence under epoxidation conditions, mixtures of another gaseous substance with at least one of the foregoing, and substances capable of forming one of the foregoing under epoxidation conditions. The oxygen is typically introduced to the reactor either as air, commercially pure oxygen or other substance which under epoxidation conditions both exists in a gaseous state and forms molecular oxygen.

The feedstream may also contain a ballast or diluent, such as nitrogen, or other inert gas, particularly when air is used as the source of oxygen. Varying amounts of water vapor may also be present.

Carbon dioxide is also desirable to include as a component of the feedstream in the epoxidation process of this invention. The presence of carbon dioxide, within certain limits, has been found to provide surprising improvement in the performance of catalysts within the scope of the invention. In particular, selectivity to propylene oxide generally will increase as the carbon dioxide concentration in the feedstream is increased. Desirable enhancements are generally observed using 1 to 60 volume % $CO_2$ in the feedstream, with 5 to 50 volume % $CO_2$ being preferred. The concentration of carbon dioxide in the feedstream may be advantageously varied during operation of the propylene epoxidation process described herein. For example, it has been found that in starting up the process using a fresh charge of catalyst, selectivity may often be significantly enhanced for an extended period of time by having carbon dioxide in the feedstream. Once the catalyst has been sufficiently conditioned to attain the desired level of performance, $CO_2$ feed may be discontinued or interrupted.

The gaseous components which are supplied to the reaction zone, or that region of the reactor where reactants and catalyst are brought together under epoxidation conditions, are generally combined before being introduced to the reactor. If desired, however, such components may alternatively be introduced separately or in various combinations. The feedstream having the particular composition previously described thus may be formed prior to or at the time the individual components thereof enter the reaction zone. The feedstream may utilize or incorporate a recycle stream from the reactor. The use of the term "feedstream" herein thus is not meant to limit the present process to the embodiment where all of the gaseous components are combined prior to introduction of said components into the reaction zone. The reactors in which the process and catalyst of the present invention are employed may be of any type known to the art. A brief description of several of the reactor parameters which may be used in the present invention is presented below.

The components of the feedstream are most suitably present in the amounts shown in the following table:

| Component | Volume in % (or ppm) for Propylene Oxidation |
|---|---|
| propylene | about 2 to about 50% |
| oxygen | about 2 to about 10% |
| organic halide | 0 to about 2,000 ppm, more preferably, <1 ppm, most preferably, 0 |
| nitrogen oxide species | 0 to about 2,000 ppm |
| hydrocarbon other than propylene | 0 to about 80% |

-continued

| Component | Volume in % (or ppm) for Propylene Oxidation |
|---|---|
| carbon dioxide | 0 to 60%, more preferably 5 to 50% |
| nitrogen or other ballast gas | remainder. |

Although the present invention can be used with any size and type of vapor phase epoxidation reactor, including both fixed bed and fluidized bed reactors known to the art, it is contemplated that the present invention will find most widespread application in standard fixed bed, multi-tubular reactors such as those now in use as ethylene oxide reactors. These generally include wall-cooled as well as adiabatic or non-wall-cooled reactors. Tube lengths may typically range from about 5 to about 60 feet but will frequently be in the range of from about 15 to about 45 feet. The tubes may have internal diameters from about 0.5 to about 2.5 inches and are expected to be typically from about 0.8 to about 1.5 inches. A plurality of tubes packed with catalyst arranged in parallel within a suitable shell may be employed. GHSV generally range from about 500 to about 10,000 hr$^{-1}$. Typically GHSV values range from about 800 to about 3,000 hour$^{-1}$ at pressures from about 1 to about 60 atmospheres, commonly about 1.1 to about 30 atmospheres. Contact times should be sufficient to convert 0.5 to 70%, preferably 5 to 30%, of the propylene.

EXAMPLES

Example 1

This example demonstrates the preparation and use of a supported silver catalyst in accordance with the invention. Calcium carbonate (25.7 g) is combined with silver chloride (1.8 g), silver oxide (35.6 g), ammonium molybdate (0.6 g), ethylene-diamine (20.56 g), oxalic acid (20.60 g), ethanolamine (7.20 g), and distilled water (27.90 g) and the resulting mixture ball milled for 4 hours. After drying for 1 hour at 110° C., the impregnated support was calcined at 300° C. for 3 hours. Thereafter, a solution of potassium nitrate (2.8 g) in water (80 mL) was mixed with the calcined material for 20 minutes on a rotary evaporator. The final supported silver catalyst was obtained by drying at 110° C. for 2 hours. The catalyst's elemental composition was 54 wt. % Ag, 19 wt. % Ca, 1.1 wt. % K, 0.55 wt. % Mo, 0.94 wt. % N, and 0.50 wt. % Cl. The epoxidation performance of the catalyst was evaluated in a fixed bed reactor at 1200 hr$^{-1}$ GHSV, 250° C., 4 mol % propylene and 8 mol % O$_2$ with no nitrogen oxide species, alkyl halide or carbon dioxide in the feedstream. The results obtained are summarized in the following table.

| Time on Stream (Min) | P (psig) | PO sel (%) | C3 = conv. (%) | PO prod. (lbPO/ft$^3$hr) | PO exit (ppm) |
|---|---|---|---|---|---|
| 0 | 30 | 45 | 21 | 0.65 | 3750 |
| 1350 | 100 | 45 | 25 | 0.75 | 4200 |

As compared to catalysts of similar composition calcined at 500° C. (see Example 2 below), the aforedescribed catalyst broke-in more quickly and appeared to have better overall performance.

Example 2

The procedure of Example 1 was repeated, except that the calcination temperature was increased to 500° C. The catalyst obtained had the following elemental composition:

| Element | Wt. % |
|---|---|
| Mo | 0.49 |
| Cl | 0.70 |
| Ca | 15.0 |
| Ag | 49.0 |
| N | 0.21 |
| K | 0.57 |

The epoxidation performance of the catalyst thus prepared was evaluated in a fixed bed reactor at 30 psig using a feedstream containing 8 vol. % propylene, 8 vol. % of oxygen, and varying amount of gaseous additives. The results obtained are shown in the following table.

| Temp (°C.) | Time on Stream (Min) | NO (ppm) | EtCl (ppm) | CO$_2$ (mol %) | GHSV (hr$^{-1}$) | PO sel (%) | C$_3$= conv. (%) | PO prod. (lb PO/ft3 hr) | PO exit (ppm) |
|---|---|---|---|---|---|---|---|---|---|
| 250 | 0 | 0 | 0 | 0 | 2400 | 34 | 6 | 0.61 | 1700 |
| 250 | 4400 | 0 | 0 | 10 | 2400 | 58 | 1.5 | 0.29 | 800 |
| 250 | 5580 | 0 | 0 | 10 | 1200 | 58 | 3.5 | 0.27 | 1500 |
| 250 | 5850 | 0 | 5 | 10 | 1200 | 58 | 3.5 | 0.27 | 1500 |
| 250 | 6300 | 5 | 5 | 10 | 1200 | 52 | 4 | 0.27 | 1500 |
| 250 | 7290 | 5 | 5 | 10 | 2400 | 64 | 1.5 | 0.40 | 1100 |
| 240 | 7650 | 5 | 5 | 10 | 2400 | 60 | 2.5 | 0.40 | 1100 |

These runs demonstrate that the catalysts of this invention are capable of selectively catalyzing the formation of propylene oxide even in the absence of ethyl chloride or nitric oxide in the feedstream. Introducing such additives into the feedstream did not substantially alter the performance of the catalyst.

Example 3

A silver catalyst supported on calcium carbonate was prepared in accordance with the invention having an elemental composition (as calculated by the reagent proportions used) corresponding to 50 wt. % Ag, 0.5 wt. % Mo (derived from molybdenum pentachloride), 0.6 wt. % Cl (derived from molybdenum pentachloride), 2 wt. % K (derived from potassium nitrate, added to the catalyst after calcination).

The effects of having gaseous promoters in the feedstream and of pretreating with a gaseous organic chloride (ethyl chloride) prior to use as in propylene oxidation were studied for catalysts of the above description. Ethyl chloride pretreatment was performed in Run A under the following conditions: 500 ppm EtCl, 5 vol. % O$_2$, balance N$_2$, 250° C., 30 psig, 1200 hr$^{-1}$ GHSV, 20 hrs. No ethyl chloride pretreatment was carried out in Run B. The results obtained are summarized in Table 1. Runs A-2 and B-2 were continuations of Runs A-1 and B-1, respectively, wherein carbon dioxide feed was discontinued after some period of time. All runs were performed at 250° C., 30 psig, and 1200 hr$^{-1}$ GHSV using a feedstream containing 10 volume % propylene and 6 volume % oxygen.

A comparison of Run A-1 with Run B-1 and Run A-2 with Run B-2 shows that pretreatment with ethyl chloride had little or no effect on catalyst performance; the use of a catalyst modified with an inorganic chloride promoter thus makes it possible to eliminate a catalyst pretreatment step.

| Run | EtCl Pretreatment | $CO_2$, Vol. % | Time on Stream, hr. | Propylene Conversion, % | Propylene Oxide Selectivity, % | PO Productivity, lb/ft$^3$ hr |
|-----|-------------------|----------------|---------------------|-------------------------|--------------------------------|-------------------------------|
| A-1 | Yes | 12 | 16 | 5 | 49 | 0.5 |
| A-2 | Yes | 0 | 64 | 9 | 35 | 0.6 |
| B-1 | No | 16 | 88 | 5 | 47 | 0.5 |
| B-2 | No | 0 | 114 | 11 | 36 | 0.8 |

Example 4

A calcium carbonate supported silver catalyst was prepared having an elemental composition corresponding to 50 weight % Ag, 2 weight % K (from $KNO_3$, added sequentially after calcination) and 0.6 weight % Cl (from AgCl). Using a feedstream containing 10 vol. % propylene, 5 vol. % $O_2$ and 200 ppm NO at 250° C. and a GHSV of 1200 hr$^{-1}$, propylene conversion was 11%, propylene oxide selectivity was 30%, and propylene oxide productivity was 0.61 lb/ft$^3$•hr.

To demonstrate the benefits of including an inorganic chloride promoter in the catalyst, a comparative epoxidation run was performed under the same conditions using a supported silver catalyst prepared without any AgCl or other source of chloride (40 weight % Ag, 2 weight % K, added as $KNO_3$ by co-impregnation). The performance of the catalyst was inferior in every respect to the AgCl-modified catalyst: 4.8% propylene conversion, 3.6% propylene oxide selectivity, 0.03 lb/ft$^3$•hr propylene oxide productivity.

Example 5

The preparation of a tungsten-promoted supported silver catalyst modified with an inorganic chloride compound is illustrated by this example. Calcium carbonate (34.0 g) was combined with silver chloride (1.3 g), silver oxide (25.75 g), ammonium tungstate oxide (0.5 g), ethylenediamine (20.56 g), oxalic acid (20.6 g), ethanolamine (7.20 g) and distilled water (27.9 g) and the resulting mixture ball milled for 4 hours. After drying 1 hour at 110° C., the impregnated supported was calcined at 300° C. for 3 hours. Thereafter, a solution of potassium nitrate (3.2 g) in water (80 mL) was mixed with the calcined material for 20 minutes on a rotary evaporator. The final supported silver catalyst was obtained by drying at 110° C. for 2 hours. Elemental composition by analysis was as follows: 41 wt. Ag, 22 wt. % Ca, 2.1 wt. % K, 0.7 wt. % W, 0.5 wt. % Cl, and 0.96 wt. % N.

The epoxidation performance of the catalyst was evaluated in a back-mixed reactor at 232° C., 1200 hr$^{-1}$ GHSV, and 30 psig using a feedstream containing 4 vol. % propylene, 8 vol. % oxygen and 10 ppm NO. Propylene conversion was 20%, selectivity to propylene oxide was 42%, and the PO productivity was 0.65 lb/ft$^3$•hr (3500 ppm PO in exit stream). A fixed bed run using the same catalyst at 288° C., 4800 hr$^{-1}$ GHSV and 30 psig (same feedstream composition, except with 50 ppm NO) yielded 22% propylene conversion, 29% propylene oxide selectivity, and a PO productivity of 2.0 lb/ft$^3$•hr (2500 ppm PO in exit stream).

Example 6

The preparation of a rhenium-promoted supported silver catalyst modified with an inorganic chloride compound is illustrated by this example. Calcium carbonate (12.85 g) was combined with silver chloride (0.9 g), silver oxide (17.80 g), ammonium perrhenate (0.41 g), potassium carbonate (1.55 g), ethylene diamine (10.28 g), oxalic acid (10.30 g), ethanolamine (3.20 g) and distilled water (14.0 g) and the resulting mixture ball milled for 4 hours. After drying for 1 hour at 110° C., the impregnated supported was calcined at 300° C. for 3 hours. The elemental composition of the catalyst by analysis was as follows: 50 wt. % Ag, 0.5 wt. % Re, 2 wt. % K and 0.6 wt. % Cl.

The epoxidation performance of the catalyst was evaluated in a fixed bed reactor at 250° C., 1200 hr$^{-1}$ GHSV and 30 psig using a feedstream containing 10 vol. % propylene, 5 vol. % oxygen, and 200 ppm NO. Propylene conversion was 10.9%, propylene oxide selectivity was 42.4%, and PO productivity was 0.9 lb/ft$^3$•hr (4740 ppm PO in exit stream).

We claim:

1. A process for propylene epoxidation comprising contacting a feedstream comprising propylene and oxygen with a supported silver catalyst comprised of:

(a) a support comprised of an alkaline earth metal compound selected from the group consisting of alkaline earth metal carbonates, alkaline earth metal titanates, and mixtures thereof;

(b) a catalytically effective amount of metallic silver;

(c) a promoting amount of an inorganic chloride promoter; and (d) a promoting amount of a potassium promoter derived from a potassium salt comprising potassium cation and a nitrogen oxyanion or precursor thereof.

2. The process of claim 1 wherein the inorganic chloride promoter is derived from an inorganic chloride compound selected from the group consisting of alkali metal chlorides, alkaline earth metal chlorides, transition metal chlorides, and mixtures thereof.

3. The process of claim 1 wherein the feedstream is essentially free of organic halide.

4. The process of claim 1 wherein the alkaline earth metal compound is selected from the group consisting of calcium carbonate, calcium titanate, and mixtures thereof.

5. The process of claim 1 wherein the feedstream is additionally comprised of a nitrogen oxide species.

6. The process of claim 1 wherein the feedstream is additionally comprised of carbon dioxide.

7. The process of claim 1 wherein the potassium salt is selected from the group consisting of potassium carbonate, potassium bicarbonate, potassium nitrate, potassium nitrite, and mixtures thereof.

8. The process of claim 1 wherein said contacting is performed at a temperature of from 180° C. to 320° C.

9. The process of claim 1 wherein the supported silver catalyst has an elemental composition corresponding to 10 to 60 weight percent Ag, 0.05 to 2 weight percent Cl, and 0.5 to 10 weight percent K and is comprised of at least 25 weight percent of the alkaline earth metal compound.

10. The process of claim 1 wherein the supported silver catalyst is additionally comprised of a promoting amount of a metal promoter selected from the group consisting of Mo, Re, W and mixtures thereof.

11. The process of claim 1 wherein the supported silver catalyst is prepared by impregnating the support with a silver compound, an inorganic chloride compound, and the potassium salt and thereafter calcining the impregnated support under conditions effective to reduce at least a portion of the silver compound to metallic silver.

12. The process of claim 1 wherein the supported silver catalyst is prepared by impregnating the support with a silver compound and an inorganic chloride compound, calcining the impregnated support under conditions effective to reduce at least a portion of the silver compound to metallic silver, and impregnating the calcined support with the potassium salt.

13. The process of claim 1 wherein the inorganic chloride promoter is derived from a transition metal chloride selected from the group consisting of silver chloride, molybdenum pentachloride, and mixtures thereof.

14. A process for propylene epoxidation comprising contacting a feedstream comprising propylene and oxygen at a temperature of from 200° C. to 300° C. with a supported silver catalyst comprised of:

(a) a support comprised of calcium carbonate;

(b) a catalytically effective amount of metallic silver;

(c) a promoting amount of an inorganic chloride promoter derived from an inorganic chloride compound selected from the group consisting of alkali metal chlorides, alkaline earth metal chlorides, transition metal chlorides and mixtures thereof; and (d) a promoting amount of a potassium promoter derived from a potassium salt selected from the group consisting of potassium carbonate, potassium bicarbonate, potassium nitrate, potassium nitrite, and mixtures thereof.

15. The process of claim 14 wherein the inorganic chloride compound is a transition metal chloride selected from the group consisting of silver chloride, molybdenum chloride, and mixtures thereof.

* * * * *